(12) United States Patent
Mardiguian

(10) Patent No.: US 6,384,021 B1
(45) Date of Patent: May 7, 2002

(54) HEPARIN COMPOSITIONS OF VERY LOW MOLECULAR WEIGHT

(75) Inventor: Jean Mardiguian, La Varenne (FR)

(73) Assignee: Laboratorios Farmaceuticos Rovi (ES)

( * ) Notice: Subject to any disclaimer, the term of this patent is extended or adjusted under 35 U.S.C. 154(b) by 0 days.

(21) Appl. No.: 09/433,409

(22) Filed: Nov. 3, 1999

(30) Foreign Application Priority Data

Jul. 23, 1999 (ES) ............................... 9901671

(51) Int. Cl.$^7$ ..................... A61K 31/715; C08B 37/10
(52) U.S. Cl. ............................ 514/56; 536/21
(58) Field of Search ................. 514/56; 536/21

(56) References Cited

U.S. PATENT DOCUMENTS

| | | | |
|---|---|---|---|
| 4,981,955 A | | 1/1991 | Lopez ..................... 536/21 |
| 6,001,820 A | * | 12/1999 | Hirsh et al. ............... 514/56 |
| 6,075,013 A | * | 6/2000 | Weitz et al. .............. 514/56 |
| 6,103,705 A | * | 8/2000 | Uzan et al. ............... 514/56 |
| 6,197,943 B1 | * | 3/2001 | Casu et al. ............... 536/21 |

* cited by examiner

Primary Examiner—Kathleen K. Fonda
(74) Attorney, Agent, or Firm—Ostrolenk, Faber, Gerb & Soffen,LLP

(57) ABSTRACT

Compositions of heparins of very low molecular weight, with the formula I, in which, n may vary between 1 and 12; $R_1$=H or $SO_3Na$; $R_2=SO_3Na$ or $COCH_3$. Such compositions of heparin are composed of mixtures of oligosaccharides or fragments of heparin and are characterised by having anti-Xa activity and anti-factor IIa activity and because they can be used as anti-thrombic medicaments.

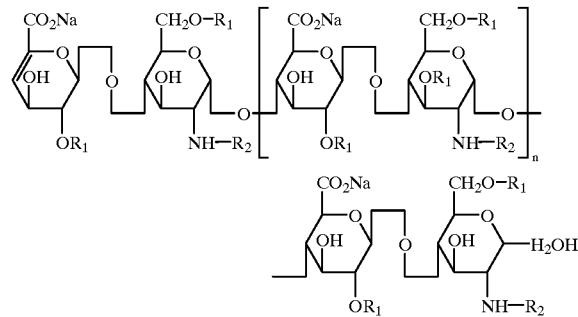

7 Claims, No Drawings

HEPARIN COMPOSITIONS OF VERY LOW MOLECULAR WEIGHT

BACKGROUND OF THE INVENTION

This invention relates to new compositions of heparins of low molecular weight (HLMW) constisting of a limited number of heparin fragments that have a 4-enopyranosyl uronate group at its non-reducing end.

Herapin is a mucopolysaccharide sulphate of animal origin, extracted from mammal intestine or lung (cow, lamb, pig) and used for some time now in human therapy for prevention and treatment of thromboembolic diseases. It is well known that the use of heparin is accompanied by very upsetting haemorrhaging effects and its daily administration, three subcutaneous or intravenous injections, constitutes a very considerable drawback.

During the course of the last few years different chemical methods have been used for depolymerising heparin, such as:

treatment with sodium nitrite in acid medium alkali treatment of esters use of free radicals generated in the presence of oxygenated water treatment of an quaternary ammonium salt of heparin in non-aqueous medium with a strong base according to a beta-elimination mechanism.

These methods allow variable yields to be obtained, mixtures of fragments of heparin in which the average molecular weight and the anti-coagulant activity vary according to the procedure and the conditions of the operation. The heparins of low molecular weight (HLMW) described in the state of the art or commercialised are obtained according to different depolymerisation procedures. Their average molecular weight (Mw) lies between 4,000 and 6,000 Daltons.

Currently it is recognised that the anti-thrombic activity of HLMW's is due principally to their capacity for activating anti-thrombin III, a plasma protein and potent inhibition of activated factor X and thrombin. In this way it is possible to measure the anti-thrombic activity of heparin by means of tests specific to the inhibition of these factors.

The research carried out by different authors in recent years shows that fragments of oligosaccharides of heparin consisting of short chains of medium molecular weight <4,800 Daltons have a selective action on activated factor X and have little effect on the global coagulation measured using methods of the farmacopea. It has been found that if fragments of very low molecular weight are required that have a strong anti Xa activity, it is preferable to use a selective depolymerisation technique in non-aqueous medium, as is described in the patent U.S. Pat. No. 4,981, 955 that does not run the risk of attacking the site of binding to anti-thrombin III.

DESCRIPTION OF THE INVENTION

In view of the background and state of the art described above, the present application has developed, using a procedure in non-aqueous medium, the controlled depolymerisation of heparin that allows a new family of HLMW to be obtained rich in oligosaccharides of low molecular weight that have a high anti-Xa activity and a low anti IIa activity, and that can be represented by the general formula:

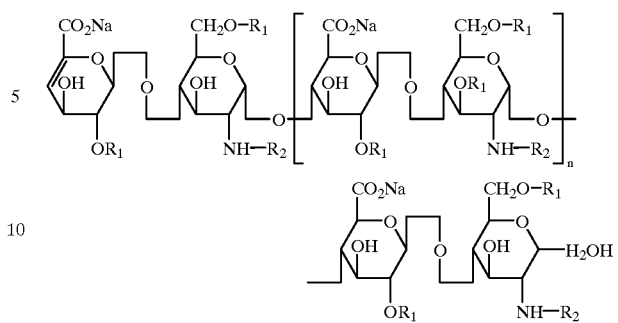

in which:

n can vary between 1 and 12

$R_1$=H or $SO_3Na$ $R_2$=$SO_3Na$ or $COCH_3$

Said heparin of very low molecular weight is obtained by selectively depolymerising the heparin in non-aqueous medium according to a procedure of beta elimination.

The compositions of heparins of very low molecular weight according to this invention are characterised by a molecular weight lying between 2,000 and 4,000 Daltons, an anti factor Xa activity of at least equal to 100 I.U./mg and contain a strong proportion, up to 75%, of oligosaccharides of low degree of polymerisation that go from hexasaccharide (n=1) to dodecasaccharide (n=4). These compositions are useful in the prophylaxis and treatment of venous and arterial thrombosis. They can be used as anti-thrombic medication.

The HLMW known and exploited commercially contain small proportions of oligosaccharides of low molecular mass, notably the oligosaccharides whose degree of polymerisation goes from hexasaccharide to dodecasaccharide.

The compositions of heparin, fruit of the present invention, have as a main characteristic, the fact that they contain a strong proportion, up to 75%, of such oligosaccharides. Furthermore, these oligosaccharides have a high anti Xa activity (>100 I.U./mg) giving them a long lasting and high anti-thrombic activity. Said compositions of heparin have an anti-Xa activity lying between 100 and 150 I.U./mg and whose anti-factor Ia activity is less than or equal to 10 I.U./mg.

The average molecular weight of the compositions of heparin of the present application lie between 2,000 and 4,000 Daltons and because:

they contain from 25 to 60% of oligosaccharides of molecular weight less than 2,000 Daltons;

they contain from 40 to 75% of oligosaccharides of molecular weight lying between 2,000 and 6,000 Daltons; and they contain less than 15% of oligosaccharides of molecular weight greater than 6,000 Daltons.

The heparin compositions of the present invention are composed of mixtures of oligosaccharides or fragments of heparin. The percentage of fragments that form part of the present invention are as follows:

contain less than 10% of fragments in which n lies between 10 and 12;

contain from 80 to 90% of fragments in which n lies between 1 and 6; and contain less than 15% of the fragments in which n lies between 7 and 9.

The present invention is illustrated by the following examples, without these examples limiting the scope of the invention.

The molecular weight (Mw), the molecular distribution, as well as the anti-factor Xa activities have been determined according to techniques described in the monograph no. 828 "Heparin of low molecular weight" of the Third Edition of the Pharmacopea Europea.

EXAMPLE 1

After dissolving 1 kg of unfractionated sodium heparin in 7 liters of purified water, 4.4 liters of a solution of benzalconium chloride in water at 50% w/v is added to the heparin solution while stirring constantly. Water is added to make up a volume of 30 liters and allowed to decant. Next the supernatant is removed and water added to make up 30 liters and left to decant. Once decanted the supernatant is removed and the precipitate liophilised. Approximately 2.7 kg of benzalconium salt of heparin is obtained (Product A). After dissolving 100 g of product A in 300 ml of dichloromethane, Triton B is added in three lots:

25 ml of Triton B is added and the mixture left for 8 hours at 25° C.

25 ml of Triton B is added and the mixture left for 16 hours at 25° C.

25 ml of Triton B is added and the mixture left for 8 hours at 25° C.

The above solution is precipitated over 600 ml of solution of sodium acetate in methanol at 10% w/v and the precipitate collected by centrifugation with washing with methanol.

The product obtained is dissolved in 500 ml of water, neutralised with 0.1N HCl, and sodium chloride added until a concentration of 10% w/v is reached. Precipitation is effected by the addition of 1.25 liters of methanol. Next the precipitate is collected by filtration washed with methanol and dryed under vacuum at 35° C. to give 33 g of Product B, which is dissolved in water at 10% w/v. The temperature is brought to 25° C. and sodium chloride added to give a concentration of 10% w/v. Precipitation is effected by adding 2.5 volumes of methanol. The precipitate is then collected by filtration washing with methanol and drying under vacuum at 35° C. obtaining 26 g of purified product, which is dissolved in water at 5% w/v. The pH is adjusted to 6.6 using 0.1 N HCl and sodium chloride added to give a concentration of 5% w/v. Precipitation is effected by addition of 0.8 volumes of methanol. After collecting the precipitate by filtration and washing with methanol, the product is dried under vacuum at 35° C. The supernatant is precipitated with 1.6 volumes of methanol. This precipitate is collected by filtration, washing with methanol, and drying under vacuum at 35° C. At the end of the process, 22 g of product is obtained.

EXAMPLE 2

The method for obtaining Product B in example 1 is repeated. 20 g of product B are dissolved in 150 ml of water and 100 ml of a solution of benzalkonium chloride in water at 50% w/v added. Next, water is added to make the mixture up to a volume of 500 ml. The mixture is left to decant. Once decanted, the supernatant is removed, water added to make up a volume of 500 ml and the mixture left to decant. After withdrawing the supernatant, the precipitate is lyophilised to give 50 g of benzalkonium salt. 20 g of the salt obtained are dissolved in 60 ml of dichloromethane. 5 ml of Triton B are added and the mixture left for 8 hours at 35° C. Next, the above solution is precipitated over 120 ml of a solution of sodium acetate in methanol at 10% w/v and the precipitate collected by centrifugation washing with methanol. The product obtained is dissolved in 100 ml of water, neutralised with 0.1N HCl, and sodium chloride added until a concentration of 10% w/v is reached. Precipitation is effected by addition of 250 ml of methanol. The precipitate is collected by filtration, washing with methanol, and drying under vacuum at 35° C. At the end of the process, 6.3 g of Product is obtained.

EXAMPLE 3

Initially 5 g of the product obtained in Example 2 are dissolved in water at a concentration of 5% w/v. The pH is adjusted to 6.6 with 0.1 N HCl and sodium chloride added until a concentration of 5% w/v is reached. Precipitation is effected by addition of 1.5 volumes of methanol. Next, the precipitate is collected by filtration washing with methanol and drying under vacuum at 35° C. At the end of the process, 3 g of Product is obtained.

EXAMPLE 4

The method for obtaining product B described in Example 1 is repeated. 20 g of product B are dissolved in 150 ml of water and 100 ml of solution of benzalkonium chloride in water at 50% w/v added. Water is then added to make up a volume of approximately 500 ml. After withdrawing the supernatant, water is added to make up a volume of 500 ml, and the mixture left to decant. The supernatant is withdrawn, water is added to make up a volume of 500 ml, and the mixture left to decant. After dissolving 20 g of the salt obtained above in 60 ml of dichloromethane, Triton B is added in two lots:

5 ml of Triton B is added and left standing for 8 hours at 35° C.

5 ml of Triton B is added and left standing for 16 hours at 35° C.

The above solution is precipitated over 120 ml of solution of sodium acetate in methanol at 10% w/v and the precipitate collected by centrifugation, washing with methanol. The product obtained is dissolved in 100 ml of water, neutralised with 0.1N HCl, and sodium chloride added until a concentration of 10% w/v is reached and precipitation effected by addition of 250 ml of methanol. The precipitate is then collected by filtration washing with methanol and drying under vacuum at 35° C. At the end of the process, 8.7 g of product is obtained.

EXAMPLE 5

Initially, 5 g of the product obtained in example 4 are dissolved in water at 5% w/v. The pH is adjusted to 6.6 with 0.1N HCl and sodium chloride added until a concentration of 5% w/v is reached. Next, precipitation is effected by addition of 0.93 volumes of methanol. After collecting the precipitate by filtration and washing with methanol, the product is dried under vacuum at 35° C.

The supernatant is precipitated with 2 volumes of methanol. The precipitate is collected by filtration washing with methanol and drying under vacuum at 35° C. Finally, 4 g of product are obtained.

ANALYSIS OF THE PRODUCTS

| | Anti-coagulant activity (I.U./mg) | | Molecular weight | Molecular distribution | | |
|---|---|---|---|---|---|---|
| | | | | * | ** | *** |
| | Anti Xa | Anti IIa | Mw | <2,000 | 2,000–6,000 | >6,000 |
| Product of Example no. 1 | 120 | 8 | 3,650 | 25 | 70 | 5 |
| Product of Example no. 2 | 105 | 3 | 3,195 | 35 | 55 | 11 |
| Product of Example no. 3 | 110 | 6 | 3,616 | 24 | 63 | 13 |
| Product of Example no. 4 | 100 | 4 | 2,777 | 42 | 52 | 7 |
| Product of Example no. 5 | 100 | 2 | 2,161 | 57 | 41 | 2 |

\* % of oligosaccharides of molecular mass less than 2,000 Daltons
\*\* % of oligosaccharides of molecular mass lying between 2,000 and 6,000 Daltons
\*\*\* % of oligosaccharides of molecular mass greater than 6,000 Daltons

What is claimed is:

1. Composition of heparin of very low molecular weight, having an anti Xa activity between 100 and 150 I.U./mg and an anti-factor IIa activity less than or equal to 10 I.U./mg, with the following general formula:

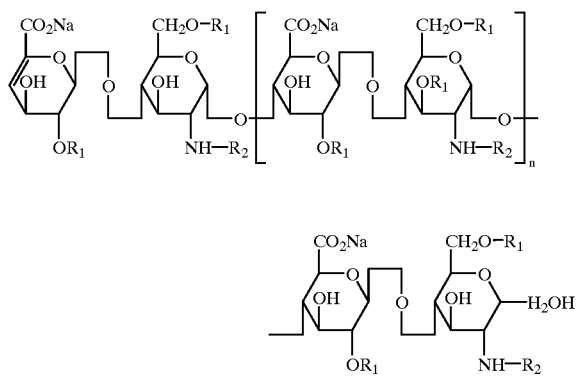

in which n is between 1 and 12
$R_1$=H or $SO_3Na$ and
$R_2$=$SO_3Na$ or $COCH_3$.

2. Composition of heparin according to claim 1, being a mixture of oligosaccharides or heparin fragments.

3. Composition of heparin according to claim 1, containing less than 10% of fragments in which n lies between 10 and 12; from 80 to 90% of fragments in which n lies between 1 and 6; and less than 15% of the fragments in which n lies between 7 and 9.

4. Composition of heparin according to claim 1, having an average molecular mass (Mw) between 2,000 and 4,000 Daltons and containing from 25 to 60% of oligosaccharides of molecular mass less then 2,000 Daltons, from 40 to 75% of oligosaccharides of molecular mass lying between 2,000 and 6,000 Daltons and less than 15% of oligosaccharides of molecular mass greater than 6,000 Daltons.

5. An anti-thrombic medicament which comprises an effective anti-thrombic amount of a composition of heparin according to claim 1.

6. An anti-thrombic medicament which comprises an effective anti-thrombic amount of a composition of heparin according to claim 3.

7. An anti-thrombic medicament which comprises an effective anti-thrombic amount of a composition of heparin according to claim 4.

* * * * *